(12) United States Patent
Nathoo

(10) Patent No.: US 8,071,076 B2
(45) Date of Patent: Dec. 6, 2011

(54) ORAL LUBRICATING AND STAIN RETARDING COMPOSITIONS

(75) Inventor: Salim A. Nathoo, Piscataway, NJ (US)

(73) Assignee: Oral Health Clinical Services LLC, Piscataway, NJ (US)

( * ) Notice: Subject to any disclaimer, the term of this patent is extended or adjusted under 35 U.S.C. 154(b) by 1250 days.

(21) Appl. No.: 10/300,624

(22) Filed: Nov. 21, 2002

(65) Prior Publication Data

US 2004/0101489 A1 May 27, 2004
US 2006/0062743 A9 Mar. 23, 2006

Related U.S. Application Data

(63) Continuation-in-part of application No. 10/155,951, filed on May 28, 2002, now abandoned, and a continuation-in-part of application No. 10/155,952, filed on May 28, 2002, now abandoned.

(51) Int. Cl.
*A61K 8/00* (2006.01)
*A61K 8/18* (2006.01)
*A61K 31/08* (2006.01)
*A61K 8/21* (2006.01)
*A61K 8/30* (2006.01)
*A61K 6/00* (2006.01)
*A61Q 11/00* (2006.01)
*A01N 31/14* (2006.01)
*C09K 3/00* (2006.01)

(52) U.S. Cl. ......... 424/49; 514/772.2; 424/52; 523/118; 106/35

(58) Field of Classification Search .................... 424/49, 424/57
See application file for complete search history.

(56) References Cited

U.S. PATENT DOCUMENTS

| | | | | |
|---|---|---|---|---|
| 3,608,069 A | * | 9/1971 | Fuller | 424/52 |
| 3,818,107 A | * | 6/1974 | Yolles | 426/3 |
| 4,482,535 A | * | 11/1984 | Sugar et al. | 424/49 |
| 4,529,535 A | * | 7/1985 | Sherman | 514/272 |
| 4,883,658 A | * | 11/1989 | Holly | 514/772.3 |
| 5,482,710 A | * | 1/1996 | Slavtcheff et al. | 424/744 |
| 5,571,501 A | * | 11/1996 | Toy | 424/49 |
| 5,651,959 A | * | 7/1997 | Hill et al. | 424/49 |
| 5,880,076 A | * | 3/1999 | Vermeer | 510/123 |
| 6,048,913 A | * | 4/2000 | Yamagishi et al. | 523/118 |
| 2002/0187181 A1 | * | 12/2002 | Godbey et al. | 424/443 |
| 2003/0039617 A1 | * | 2/2003 | White et al. | 424/49 |

OTHER PUBLICATIONS

Bragg et al. U.S. Appl. No. 60/408,953, filed Sep. 6, 2002.*
Joiner et al., Investigation of Factors Influencing Stain Formation Utilizing an in situ Model, Adv. Dent. Res. 9(4): pp. 471-476, Dec. 1995.*

* cited by examiner

*Primary Examiner* — David J Blanchard
*Assistant Examiner* — Devang Thakor
(74) *Attorney, Agent, or Firm* — Kilpatrick Townsend & Stockton LLP

(57) ABSTRACT

An oral lubricant having usefulness for alleviating the symptoms of dry mouth and preventing accumulation of dental stains based on a polyvinyl alcohol polymer containing composition in an orally acceptable carrier or vehicle. The invention relates generally to an oral composition having a function in lubricating the mouth and preventing the formation of stains on the surfaces of the teeth. The active ingredients of the composition are a polyvinyl alcohol, a metal chelating agent, lipophilic vitamin, surface active material and a phenolic anti microbial agent with anti-inflammatory properties.

26 Claims, No Drawings

ORAL LUBRICATING AND STAIN RETARDING COMPOSITIONS

CROSS-REFERENCE TO RELATED APPLICATIONS

This application is a continuation-in-part of U.S. patent application Ser. Nos. 10/155,951 and 10/155,952, filed on May 28, 2002, now abandoned.

BACKGROUND OF THE INVENTION

1. Field of the Invention

The invention relates generally to an oral composition having a function in lubricating the mouth and preventing the formation of stains on the surfaces of the teeth. The active ingredients of the composition are a polyvinyl alcohol and a metal chelating agent.

The invention also encompasses a method of treating xerostomia comprising of administering to an affected individual a lubricant composition containing an alcoholic polymer and a metal chelating agent in an orally acceptable vehicle.

2. The Prior Art

Xerostomia commonly known as "dry mouth" is a condition in which the salivary glands do not produce sufficient quantities of saliva. This causes discomfort that can in some cases be quite severe. Without saliva, the mouth burns and the throat and tongue can undergo physiological changes. Teeth can also decay rapidly and the tongue can become smooth, cracked and vulnerable to infection.

The mouth is one of the body areas most exposed to the external environment. Normally, mucous forms a continuous protective layer in the nose, mouth and throat. A patient suffering from xerostomia not only has decreased fluid in the mouth, but also an insufficient quantity of mucoproteins and mucopolysaccharides to hold fluid in contact with the cells and create a barrier to irritation and infection.

Cases of xerostomia may vary from the mild, in which only slight dryness is experienced, to severe cases in which the patient will have serious problems with mastication, swallowing, digestion, speech, and the like. As noted in U.S. Pat. No. 4,438,100 to Balslev et al., there is a number of causes of xerostomia, including the physiological (e.g., age, menopause, postoperative conditions, dehydration), as well as the psychological (nervousness). The reasons for mouth dryness may also be pharmacological (e.g., as a common side effect of many medications, including anti hypertensives, diuretics, anti-arthritics and anti-depressants) or as a result of radiotherapy. The most severe cases of xerostomia are caused by radiation therapy after head and neck surgery and by autoimmune diseases such as lupus, Sjogrens Syndrome, and rheumatoid arthritis.

Until recently, the treatments for xerostomia have had significant drawbacks. For example, symptoms of mild xerostomia can be somewhat alleviated by consumption of fluids, hard candy and throat lozenges. Because of the susceptibility of xerostomia patients to tooth decay and gum disease, however, the increased sugar intake associated with conventional candy and lozenges is of real concern. In addition, fluids or candy are typically not effective with more severe cases of xerostomia, nor do they provide long-lasting relief with mild cases.

Artificial saliva and salivary substitutes have been proposed as palliative treatments for the symptoms of xerostomia, which preparations have physical and chemical properties that simulate those of natural (human) saliva.

Artificial salvias of the prior art include compositions, which contain ions that mimic those found in natural saliva; glycerin, as well as carboxymethylcellulose-based preparations to provide the proper level of viscosity. Fluoride ions are sometimes included to prevent demineralization of tooth enamel. These compositions have not found wide acceptance as many patients find, that such preparations are irritating or distasteful, and that their lubricating effect is of relatively short duration. This lack of wide acceptance is believed due, at least in part to the fact that the artificial saliva preparations of the prior art do not fully possess the rheological characteristics of natural saliva which are responsible for natural saliva's lubricating effect. An article entitled "Lubrication and Viscosity Features of Human Saliva and Commercially Available Saliva Substitutes", M. N. Hatton et al, J. Oral Maxillotac. Surg. 45, 496-499 (1987), contains a full discussion of the problems associated with the presently available commercial saliva substitutes in the treatment of individuals with diminished salivary gland function.

In view of the problems, which occur when salivary secretion is deficient, it will be understood that it would be most desirable to have an oral lubricating composition for human use, to relieve the above-mentioned discomforts and inconveniences incurred by xerostomia or by a greater or lesser tendency to dryness of the mouth. Such a composition should have lubricating properties which are as close to the properties of the natural saliva so as to provide to the patient long-term relief from the symptoms of xerostomia or dry mouth.

The uses of lubricating polymers are well known the ophthalmic area. For example, U.S. Pat. No. 4,529,535 to Sherman discloses a rewetting solution that is particularly useful for rigid silicone copolymer contact lenses, including extended wear lenses. In one embodiment, the rewetting solution contains the combination of hydroxyethylcellulose, polyvinyl alcohol, and polyvinylpyrrolidone. U.S. Pat. No. 4,748,189 to Su et al. discloses ophthalmic solutions for improving the exchange of fluid in the area outside a hydrogel contact lens in the area underneath the hydrogel contact lens, in order to permit tear exchange to occur, thereby preventing the accumulation of waste matter and debris under the lens. The solution contains a hydrogel-flattening agent, for example urea, glycerin, propylene glycol, sorbitol, or an amino-ethanol. Surfactants that are useful in the solution include poloxamer and tyloxapol. Suitable lubricants include hydroxylethylcellulose, polyvinylalchol, and polyvinylpyrrolidone.

For a lubricating polymer to be useful in the oral cavity it should be non-irritating and have adhesive properties. Various polymers have been proposed for use in establishing adhesive contact with mucosal surfaces. See, for example, Biegajski, U.S. Pat. No. 5,700,478 to Lowey, U.S. Pat. No. 4,259,314 to Lowey, U.S. Pat. No. 4,680,323 to Yukimatsu et al., U.S. Pat. No. 4,740,365 to Kwiatek et al., U.S. Pat. No. 4,573,996 to Suzuki et al., U.S. Pat. No. 4,292,299 to Suzuki et al., U.S. Pat. No. 4,715,369 to Mizobuchi et al., U.S. Pat. No. 4,876,092 to Fankhauser et al, U.S. Pat. No. 4,855,142; Nagai et al., U.S. Pat. No. 4,250,163 to Nagai et al., U.S. Pat. No. 4,226,848 to Browning, U.S. Pat. No. 4,948,580 to Schiraldi et al. Typically, these adhesives consist of a matrix of a hydrophilic, e.g., water soluble or swell able, polymer or mixture of polymers which can adhere to wet mucosal surfaces. Such polymers are inclusive of hydroxypropyl cellulose, hydroxypropyl methylcellulose, hydroxy ethylcellulose, ethylcellulose, carboxymethyl cellulose, dextran, gaur-gum, polyvinyl pyrrolidone, pectins, starches, gelatin, casein, acrylic acid, acrylic acid esters, acrylic acid copolymers, vinyl polymers, vinyl copolymers, vinyl alcohols, alkoxy polymers, polyethylene oxide polymers, polyethers, and the like. These adhesives may be formulated as ointments, thin films, tablets, troches, and other forms. Often, these adhesives have had medicaments mixed therewith to effectuate slow release or local delivery of a drug rather then treat xerostomia or dry mouth.

Some of the polymers described above have several drawbacks. For example materials such as Carbopol (carboxyvinyl polymers), are not water soluble thus leave a tacky, greasy residue in the oral cavity of the wearer, and can cause sustained oral irritation and some forms of adhesives remain in the oral cavity for only short periods of time, e.g. generally not more than about 10 or 20 minutes, and therefore cannot provide for delivery of a substance over an extended period of time.

U.S. Pat. No. 5,886,054 discloses a composition to treat xerostomia, which comprises of an aqueous solution of at least one polymer and at least one electrolyte, wherein the aqueous solution is preferably buffered and optionally contains at least one mucin. The polymer can be chosen for instance from the group which consists of scleroglucan, guar gum, xanthan gum, sodium carboxymethyl cellulose, hydroxyethyl cellulose, polyacrylic acid and polyvinyl alcohol. The therapeutic composition according to the invention can serve as saliva substitution agent, artificial tear water, in a mouth rinse or in a toothpaste. The aforementioned patient teaches that the mucin is critical because saliva mucins can adhere to both the surface of the teeth and to the oral mucosa and polyacrylic acid subsequently binds to the mucin in order to form a protective layer.

For a lubricant to be effective, it has to interact with the surfaces it is protecting. Referring to U.S. Pat. No. 5,886,054, the disadvantage of combining polyvinyl alcohol with an electrolyte is that the cation may interact with the polymer and cause precipitation of polyvinyl alcohol. Further, saliva is known to contain high concentrations of electrolytes, which may cause further precipitation of polyvinyl alcohol thus leaving a granular feeling in the mouth. Hence, the addition of a metal chelating agent to a formulation containing polyvinyl alcohol will aid in its anti-xerostomia properties. Further inclusion of salivary mucins have other disadvantages including; the mucins are biopolymers which are difficult to obtain in sufficient quantities and suitable purity, they are expensive and they may be obtained from animal salivary glands which may make the use of mucin unsuitable for some consumers and patients. Hence, there is a need to develop products that will retain moisture in the oral cavity that will be inexpensive, and will be acceptable to a majority of consumers. It will also be beneficial to develop products that have added benefits such as prevention of dental stains or accumulation of unaesthetic materials on tooth surfaces and also to prevent irritation/inflammation occurring as a result of dry mouth.

SUMMARY OF THE INVENTION

Polyvinyl alcohols also referred to as polyhydroxy polymers are well known for their excellent adhesion to hydrophilic materials. Currently, as indicated above they are used for lubricating eyes. The use of polyvinyl alcohols for treating dry eyes has been detailed in U.S. Pat. No. 4,883,658, which teaches that polyvinyl alcohols interact with corneal surfaces and adsorbs fairly tenaciously so that it cannot be easily rinsed off from solid surfaces, related to the eyes. Further, U.S. Pat. No. 4,883,658 teaches that two types of polyvinyl alcohols are necessary to provide a stable lubricating film. Polyvinyl alcohol with high acetate content (but not more than 27%) is quite surface active and is capable of lowering the surface tension of water from 72 to 42 mN/m. On the other hand, polyvinyl alcohol that is fully hydrolyzed exhibits almost no surface activity at the water-air interface. In general, the lower the surface tension of a liquid, the more it will wet a given solid surface. It has now surprisingly been found that formulations containing a polyhydroxy polymer are effective in lubricating the mouth and have an added benefit of preventing the accumulation of stain on tooth surfaces.

It is not understood why the inventive compositions are effective at both lubricating the mouth and preventing the accumulation of dental stain. Without being bound to a particular theory it is thought that polyhydroxy polymer coats the surfaces of the teeth thus providing a physical barrier onto which stains may adhere. This is in contrast to the normal stain formation mechanism whereby the materials directly adhere to the surfaces of the teeth. The lubricating action of the inventive composition my also be related to the adsorption of the polyvinyl alcohol to the mucosal surfaces.

Thus, the object of the present invention is to provide a composition and a method for lubricating the tissues of the mouth and at the same time preventing the accumulation of stain on tooth surfaces. The composition consists of formulating of a polyvinyl alcohol, metal chelating agents and a fat soluble vitamin. Surface active materials are also included aid in the solubilization of surface debris and to further reduce the surface tension in order to assist in the formation of a lubricating and a protective film on the surfaces of the teeth and the mucosal surfaces.

Anti-inflammatory agents can also be added to the composition to provide relief from irritation arising from mouth dryness.

The inventive composition may be administered in any orally acceptable vehicle e.g., tooth paste or mouth wash.

DETAILED DESCRIPTION OF THE PREFERRED EMBODIMENTS

Polyvinyl alcohol (PVA) is a known, commercially available polymer prepared by replacing acetate groups of polyvinyl acetates with hydroxyl groups. The alcoholysis reaction proceeds most rapidly in a mixture of methanol and methyl acetate in the presence of catalytic amounts of alkali or mineral acids. The polyvinyl alcohol and the synthesis thereof are described in greater detail by D. L. Cincera in Kirk-Othmer ENCYCLOPEDIA OF CHEMICAL TECHNOLOGY, Third Edition, John Wiley & Sons, New York (1983), Volume 23, pages 848-865.

The Air Products and Chemicals Inc sell the polyvinyl alcohol used in the composition described herein under the trademark Airvol™. It is to be understood, however, that the invention is not limited to the use of any specific polyvinyl alcohol, and that any equivalent polyvinyl alcohol of pharmaceutical grade can be used to achieve equivalent results.

The polyvinyl alcohol used in this invention composition may be either fully hydrolyzed or partially hydrolyzed material having average molecular weight ranging from 2,000 to 125,000. It is preferred to use polyvinyl alcohol having an average molecular weight of about 30,000 to 110,000. The concentration of the polyvinyl alcohol will vary according to the type of the oral care composition.

In mouth rinses and tooth paste compositions a concentration of about 0.1% to 5% w/w is preferred, whereas in a tooth gel formulations i.e. dentifrices without the abrasives a concentration of 2% to 20% is preferred. Lozenges and chewing gums may have concentrations of 0.1% to 20%.

Agents, which chelate metal ions, are essential ingredients of the present invention. The purpose of the chelating agents is to prevent sequester the metal ions which may bind to the polyvinyl alcohol and promote its precipitation and therefore interfere with the film forming capabilities. The metal chelating agents include a condensed pyrophosphate compound. For purposes of this invention "condensed phosphate," relates to an inorganic phosphate composition containing two or more phosphate species in a linear or cyclic pyrophosphate form. The preferred condensed phosphate comprises of sodium pyrophosphate but can also include tripolyphosphate, hexametaphosphate, cyclic condensed phosphate or other similar phosphates well known in the field. The metal chelating agent may also include an organic chelating agent. The term "organic phosphate" includes phosphonic acid, di and tri phosphonoc acid compound or its salts, oxalic acid and or its salts. The preferred phosphonic acid is sold under the trade name of Dequest 2010 and is called 1-hydroxyethylidene-1, 1-diphosphonic acid. The chelating agents are incorporated individually or in any combination in the oral care compositions of the present invention in an amount within the range of 0.01 to about 10.0% by weight and preferably from about 0.25% to about 3.0% by weight.

Lipophilic materials are also included in the composition. U.S. Pat. No. detailed in U.S. Pat. No. 4,883,658 teaches that polyvinyl alcohols the polymer adsorbs fairly tenaciously and can be removed by the shear action when the formation contaminated with lipids. For a surface film to be stable the shear action is important because it enables the film to move with the movement of the mucosal tissues. Hence, in order to promote the mobility of the film formed over the mucosal surfaces a safe lipophilic material is included in the composition. It is well known that people with dry mouth have irritated or inflamed mucosal tissues. The irritation may be due to oxidative damage hence; it is preferred to include lipophilic materials with anti-oxidant properties to the composition. These materials may be anti-oxidants such as butyrated hydroxy toluene or fat-soluble vitamins such as Vitamins A, D and E. The preferred lipophilic material with anti-oxidation properties is Vitamin E. The term "vitamin E" as used herein includes tocopherol (vitamin E) and derivatives thereof, for example dl-.alpha.-tocopherol, tocopherol acetate (vitamin E acetate ester), tocopherol succinate (vitamin E succinate ester), etc. As extrapharmacopoeial species, there may be mentioned, for example, alpha-tocopherol, beta-tocopherol, gamma-tocopherol, delta-tocopherol, tocopherol nicotinate (vitamin E nicotinate ester), tocopherol phosphate (vitamin E phosphate ester) and tocopherol linolenate (vitamin E linolenate ester). Vitamin E is incorporated in the formulation from about 0.01% to 3% (w/w).

Other lipophilic materials with anti-inflammatory and anti microbial activities may also be included in the composition. The purpose of adding these ingredients are that they act as preservatives of the composition due to their anti-microbial action and they can also act to control inflammation occurring as a result of mouth dryness. These agents may be selected from the following group, which includes halogenated diphenyl ethers, halogenated salicylanilides, benzoic esters, halogenated carbanalides, and phenolic compounds. The most preferred anti-inflammatory agents are substantially water-insoluble members of either the halogenated diphenyl ether group or the phenolic group, in particular those compounds described in detail in U.S. Pat. Nos. 4,894,220 and 5,800,803, which are incorporated herein by reference.

The most preferred water-insoluble or lipophilic agent (herein defined as a compound having a solubility in distilled water at 25° C. of less than 1000 ppm) is triclosan (trade name Irgasan DP300). Triclosan (2,4,4'-trichloro-2'-hydroxydiphenyl ether, CAS No. 338034-5) is a broad spectrum antimicrobial/anti inflammatory agent with a molecular weight of 289.5, having very limited water solubility at physiological temperatures (20 ppm in distilled water at 20° C. and 40 ppm in distilled water at 50° C.). The safety of triclosan has been well established and its use in oral care products, primarily water-based toothpastes in which the triclosan, typically at a concentration of about 0.30 percent by weight, has been solubilized.

According to one embodiment of the present invention, the concentration of triclosan will be at least about 0.10% percent by weight of the ingredients formulating the composition, depending upon the solubility of the antimicrobial compound in the composition. According to an alternate embodiment, the concentration of the antimicrobial agent is 0.3%. The concentration of the water-lipophilic anti-inflammatory compound will be in the range of between about 0.05 percent and about 2%.

Surfactants are also included in the inventive composition. The purpose of the surfactant is to aid in the solubilization of surface debris and to further reduce the surface tension in order to assist in the formation of a lubricating and a protective film on the surfaces of the teeth and the mucosal surfaces. The surfactant also assists in achieving thorough and complete dispersion of ingredients throughout the oral cavity and renders the compositions more cosmetically acceptable. Non-ionic surfactants also maintain the flavoring materials in solution. In addition, non-ionic surfactants are compatible with the polyvinyl alcohol polymers of its invention, providing for a stable, homogeneous composition.

The surfactants are included from about 0.5 to 50% of the weight of the composition and preferably from about 1% to about 33% by weight of the composition.

Surfactants useful in the practice of the present invention include non-ionic organic surface-active polymers such as polyoxyethylene-polyoxy-propylene block copolymers such as Pluronic 108 and Pluronic F-127 marketed by BASF. Pluronic 108 has a molecular weight of 3200 and contains 80% of the hydrophilic polyoxyethylene moiety and Pluronic F127 has a molecular weight of 4000 and contains 70% polyoxyethylene. Other surfactants include alkali metal alkyl sulfates of 8 to 20 carbon atoms, preferably of 10 to 18 and more preferably of 12 to 16 carbon atoms in the alkyls thereof such as Tween 20, which is a and sodium lauryl phosphate. The surfactants may also include sodium cocomonoglyceride sulfate, sodium linear tridecylbenzene sulfonate, N-lauroyl N-methyl taurate and nonionic surfactants such as a water soluble polyoxyethylene monoester of sorbitol with a $C_{10-18}$ fatty acid ester of sorbitol (and sorbitol anhydrides), consisting predominantly of the monoester, condensed with about 10-30, preferably about 20, moles of ethyleneoxide. The fatty acid (aliphatic hydrocarbon-monocarboxylic acid) may be saturated or unsaturated, e.g. lauric, palmitic, stearic, oleic acids. A mixed surfactant system consisting of polyoxyethylene-polyoxypropylene block copolymers (Pluronic F-108 and Pluronic F-127), polyoxyethylene (20) sorbitan monolaurate (Tween 20) and sodium lauryl sulfate is preferred however the surfactants can be used individually or in any combination thereof.

Humectants used to prepare the aqueous vehicle include glycerin, sorbitol and polyethylene glycol of molecular weight 400-2000.

Examples of preservatives useful in the practice of the present invention include benzoic acid, sodium benzoate cetylpyridinium chloride, thymol etc. Triclosan is preferred because it has been shown to have anti-inflammatory properties in addition to its anti-microbial properties.

Alcohol such as ethanol can also be included in the composition as a preservative and a flavor enhancement.

Materials that prevent dental caries such as sodium fluoride, stannous fluoride and sodium monofluorophosphate can also be included. Sweeteners suitable for use in the composition include xylitol, saccharin and sorbitol. Other compounds which provide beneficial effects such as potassium nitrate which prevents dental hypersensitivity, compounds of zinc or barium which prevent halitosis and compounds which release active oxygen such as hydrogen peroxide, carbamide peroxide and metal peroxides can also be incorporated into the composition.

A typical mouth rinse or spray prepared in accordance with the practice of the present invention contains the following ingredients in percent by weight based on the weight of the total formulation.

| Ingredient | % by Weight |
|---|---|
| Water | 77.74 |
| Glycerin | 8 |
| Xylitol | 4 |
| Polyethylene glycol 600 | 3 |
| Pluronic F-108 | 3 |
| Pluronic F-127 | 1.3 |
| Polyvinyl alcohol | 0.66 |
| Sodium pyrophosphate | 0.5 |
| Oxalic Acid | 0.5 |
| Dequest 2010 | 0.4 |
| Tween 20 | 0.4 |
| Sodium Lauryl Sulfate | 0.2 |
| Vitamin E (dl-alpha-tocopheryl acetate) | 0.1 |
| Triclosan | 0.1 |
| Flavor | 0.1 |

The mouth rinse was prepared by dispersing the polyvinyl alcohol (average molecular weight 100,000; degree of hydrolysation 86-90 mol %) in cold water with vigorous agitation. The mixture was then heated to boiling with agitation until a clear solution was obtained. Then glycerin, sodium pyrophosphate, oxalic acid and Dequest 2010 were added. After the materials were dissolved the Pluronics were added and the mixture stirred until a clear homogenous solution was obtained. Then xylitol and SLS were added. In a separate container a second mixture was prepared which contained Tween 20, polyethylene glycol, triclosan, Vitamin E and flavor. The mixture was added to the first container. To prevent excessive foaming, a safe antifoaming agent e.g., antifoam A can be added to the mixture. Further alcohol e.g., ethanol can be added if desired to improve consumer acceptability.

To examine the moisturizing effects of the mouth rinse detailed above, six subjects who complained of dry mouth were recruited to participate in the study. All subjects brushed their teeth with a leading fluoridated toothpaste, rinsed with water and then rinsed with the mouth wash shown in table 1. The subjects were then asked if their mouth felt lubricated and moisturized at 5 minutes after rinsing, 30 minutes after rinsing and one hour after rinsing. All subjects reported that their mouth felt lubricated and moisturized. Further the subjects also reported that their mouths felt cleaner. The study was then repeated using a leading mouth rinse. All the subjects reported that their mouth felt cleaner but did not have an effect on the lubricity or the "dryness" of their mouth. The data therefore, indicates that the inventive composition lubricates and moisturizes the mouth.

The mouth rinse was then tested to examine the stain prevention capabilities. Extracted human teeth were soaked in 30% hydrogen peroxide to remove all the stain. Baseline color was then measured using the Minolta chromameter. Color readings were obtained in the $L^*, a^*, b^*$ color coordinates. The teeth were then soaked for seven minutes in the mouth rinse described in the table above. The teeth were then incubated in stimulated saliva for five minutes and the color re-measured to determine if the mouthwash would prevent accumulation of pellicle and keep the teeth white. The teeth were then transferred to a chromogenic mixture containing 10% coffee, 10% tea and 2% non-dairy creamer. The incubation was performed for one hour in order to determine if the rinse would prevent stain accumulation. The teeth were then removed, placed in distilled water and the color was measured. The change in color was calculated using the standard CIE $L^*a^*b^*$ color difference equation. The results indicated that the inventive composition prevented accumulation of stain on tooth surfaces. The results are as follows:

TABLE 1

Demonstration of prevention of pellicle accumulation

| | E (whitened teeth) | E (color after incubation in mouth-rinse and saliva) | Delta E |
|---|---|---|---|
| Control | 76.88 | 75.86 | 1.02 |
| Treated | 79.52 | 79.20 | 0.32 |

In the table above control refers to treatment with a commercial mouth rinse, and treated refers to the inventive mouth rinse. The data shows that the inventive mouthwash accumulates less pellicle and keeps the teeth whiter.

TABLE 2

Demonstration of prevention of stain accumulation

| | E (whitened teeth) | E (color after incubation in mouth-rinse and stain broth) | Delta E |
|---|---|---|---|
| Control | 76.88 | 73.92 | 2.96 |
| Treated | 79.52 | 77.90 | 1.62 |

The delta E of the treated sample is lower when compared to the delta E of the control sample indicating that the inventive composition will prevent stain accumulation.

A study was then performed to examine the stain removal capability of the mouth rinse. The stained teeth above were then soaked in a commercial mouth rinse or the inventive composition for one minute and color was measured. The calculation in color change were performed using the CIE $L^*a^*b^*$ color difference equation.

TABLE 3

Demonstration of stain removal

| | E (color after mouth-rinse and stain broth incubation) | E (color after incubation in rinse) | Delta E |
|---|---|---|---|
| Control | 73.92 | 73.48 | 0.42 |
| Treated | 77.90 | 78.59 | −0.69 |

The table above shows a delta E of −0.69 of teeth after incubation in the inventive rinse indication that the rinse removes stain when compared to a popular mouth rinse.

A typical dentifrice such as a toothpaste or gel can be prepared in accordance with the practice of the present invention contains the following ingredients:

| Ingredient | % by Weight |
| --- | --- |
| Water | 54.6 |
| Polishing agent | 14 |
| Glycerin | 10 |
| Xylitol | 4 |
| Polyethylene glycol 600 | 3 |
| Pluronic F-108 | 3 |
| Silica thickener | 3 |
| Sodium Lauryl Sulfate | 1.5 |
| Carrageenan gum | 1.5 |
| Pluronic F-127 | 1.3 |
| Sodium pyrophosphate | 1 |
| Polyvinyl alcohol | 0.66 |
| Dequest 2010 | 0.4 |
| Tween 20 | 0.4 |
| Sodium Flouride | 0.24 |
| Vitamin E (dl-alpha-tocopheryl acetate) | 0.1 |
| Triclosan | 0.3 |
| Flavor | 1.0 |

Abrasives or polishing agents useful to prepare the dentifrice compositions of the present invention include finely divided silica, dicalcium phosphate, calcium pyrophosphate, sodium bicarbonate, insoluble sodium metaphosphate and tricalcium phosphate.

Thickeners include silica thickeners, carob bean gum, carrageenan gum, hydroxymethyl cellulose, hydroxypropyl cellulose alginates, gantrez, polyvinyl pyrrolidine and various carbopols Humectants include glycerol, sorbitol, propylene glycol, polypropylene glycol and/or mannitol.

Aspartame or saccharin may be used as the artificial sweetener, and the flavor may be based principally or partially on limonene and may contain menthol or other physiologically cooling agent to give it a special appeal.

What is claimed is:

1. A composition for preventing accumulation of dental stain upon surfaces of teeth, comprising:
a hydrolyzed polyvinyl alcohol polymer that forms a film on the surfaces of teeth; fluoride; a metal chelating agent; and
an orally acceptable vehicle selected from the group consisting of tooth paste, tooth gel, lozenges, chewing gum, and mouthwash.

2. The composition of claim 1 wherein the hydrolyzed polyvinyl alcohol is present at a concentration in the range of about 0.005% to about 15% by weight.

3. The composition of claim 1 wherein the metal chelating agent is selected from the group consisting of sodium pyrophosphate, sodium tripolyphosphate, sodium hexametaphosphate, phosphonic acid, di and tri phosphonic acid compound or its salts, oxalic acid or its salts, alpha hydroxy acids or their salts, and any combination thereof.

4. The composition of claim 1 wherein the metal chelating agent is present at a concentration in the range of about 0.01% to about 10.0% by weight.

5. The composition of claim 1 wherein the composition further comprises one or more fat soluble vitamins selected from the group consisting of vitamin A or its derivative, Vitamin D or its derivative, Vitamin E or its derivative, and any combination thereof and are present at a concentration in the range of about 0.01% to about 10.0% by weight.

6. The composition of claim 1 wherein the composition further comprises a surface active material.

7. The composition according to claim 6 wherein the surface active material is selected from the group consisting of ionic surfactants, non-ionic surfactants, and any combination thereof.

8. The composition according to claim 6 wherein the surface active material is one or more compounds selected from the group consisting of polyoxyethylene-polyoxypropylene block copolymers, polyoxyethylene sorbitan monolaurate, sodium lauryl sulfate, betaine, and any combination thereof and is present at a concentration in the range of about 0.25% to about 25% by weight.

9. The composition of claim 1 wherein the composition further comprises an anti-inflammatory agent having antimicrobial properties.

10. The composition of claim 9 wherein the anti-inflammatory agent is a phenolic compound.

11. The composition of claim 10 wherein the anti-inflammatory agent is triclosan.

12. The composition of claim 11 wherein the concentration of triclosan is in the range of about 0.05% to about 1.0% by weight.

13. A composition for lubricating the mouth and preventing accumulation of dental stain, comprising:
a hydrolyzed polyvinyl alcohol polymer that forms a film in an oral cavity;
fluoride; a metal chelating agent;
an orally acceptable vehicle selected from the group consisting of tooth paste, tooth gel, lozenges, chewing gum and mouthwash; and
wherein the composition is administered in an amount effective to lubricate the mouth and prevent accumulation of dental stain.

14. The composition of claim 13 wherein the polyvinyl alcohol polymer is present at a concentration in the range of about 0.005% to about 15% by weight.

15. The composition of claim 13 wherein the metal chelating agent is selected from the group consisting of sodium pyrophosphate, sodium tripolyphosphate, sodium hexametaphosphate, phosphonic acid, di and tri phosphonic acid compound or its salts, oxalic acid or its salts, alpha hydroxy acids or their salts, and any combination thereof.

16. The composition of claim 13 wherein the metal chelating agent is present at a concentration in the range of about 0.01% to about 10.0% by weight.

17. The composition of claim 13 wherein the composition further comprises one or more fat soluble vitamins selected from the group consisting of vitamin A or its derivatives, Vitamin D or its derivatives, Vitamin E or its derivatives, and any combination thereof and are present at a concentration in the range of about 0.01% to about 10.0% by weight.

18. The composition of claim 13 wherein the composition further comprises a surface active material.

19. The composition of claim 18 wherein the surface active material is selected from the group consisting of ionic surfactants, non-ionic surfactants, and any combination thereof.

20. The composition of claim 18 wherein the surface active material is one or more compounds selected from the group consisting of polyoxyethylene-polyoxypropylene block copolymers, polyoxyethylene sorbitan monolaurates, lauryl sulfates, betaines, and any combination thereof and is present at a concentration in the range of about 0.25% to about 25% by weight.

21. The composition of claim 13 wherein the composition further comprises an anti-inflammatory agent having antimicrobial properties.

22. The composition of claim 21 wherein the anti-inflammatory agent is a phenolic compound.

23. The composition of claim 22 wherein the anti-inflammatory agent is triclosan.

24. The composition of claim 23 wherein the concentration of triclosan is in the range of about 0.05% to about 1.0% by weight.

25. The composition of claim 1 wherein the metal chelating agent is present at a concentration in the range of about 0.25% to about 10.0% by weight.

26. The composition of claim 13 wherein the metal chelating agent is present at a concentration in the range of about 0.25% to about 10.0% by weight.

* * * * *